(12) United States Patent
Suzuki et al.

(10) Patent No.: US 8,205,485 B2
(45) Date of Patent: Jun. 26, 2012

(54) WAY OF METHOD TRANSFER OF LIQUID CHROMATOGRAPH AND LIQUID CHROMATOGRAPH SYSTEM

(75) Inventors: Takaaki Suzuki, Hitachinaka (JP);
Masato Fukuda, Hitachinaka (JP);
Masahito Ito, Hitachinaka (JP)

(73) Assignee: Hitachi High-Technolgies Corporation, Tokyo (JP)

( * ) Notice: Subject to any disclaimer, the term of this patent is extended or adjusted under 35 U.S.C. 154(b) by 378 days.

(21) Appl. No.: 12/470,164

(22) Filed: May 21, 2009

(65) Prior Publication Data

US 2009/0288473 A1   Nov. 26, 2009

(30) Foreign Application Priority Data

May 23, 2008   (JP) ................................. 2008-134904

(51) Int. Cl.
*G01N 30/00* (2006.01)
(52) U.S. Cl. ...................................................... 73/61.52
(58) Field of Classification Search .................. 73/61.52
See application file for complete search history.

(56) References Cited

U.S. PATENT DOCUMENTS

| | | | |
|---|---|---|---|
| 4,824,446 A | | 4/1989 | Mowery, Jr. |
| 4,982,597 A | * | 1/1991 | Berger ......................... 73/23.25 |
| 5,405,432 A | * | 4/1995 | Snyder et al. ..................... 95/82 |
| 5,476,000 A | | 12/1995 | Henderson et al. |
| 5,644,503 A | * | 7/1997 | Ito et al. ........................... 702/22 |
| 5,915,269 A | | 6/1999 | Cahill et al. |
| 5,970,425 A | | 10/1999 | Ono et al. |
| 5,987,959 A | * | 11/1999 | Klee et al. ........................ 73/1.02 |
| 6,153,438 A | | 11/2000 | Blumberg et al. |
| 6,358,692 B1 | * | 3/2002 | Jindal et al. ..................... 435/7.1 |
| 6,393,368 B1 | * | 5/2002 | Ito et al. ........................... 702/22 |
| 6,794,148 B2 | * | 9/2004 | Jindal et al. ..................... 435/7.1 |
| 7,110,886 B2 | * | 9/2006 | Ito et al. ........................... 702/22 |
| 7,356,446 B2 | * | 4/2008 | Ito et al. ......................... 702/189 |
| 7,503,340 B2 | * | 3/2009 | Klee et al. ................... 137/487.5 |
| 2002/0150926 A1 | * | 10/2002 | Jindal et al. ........................ 435/6 |

(Continued)

FOREIGN PATENT DOCUMENTS

DE    44 42 637 A1   10/1995

(Continued)

OTHER PUBLICATIONS

European Search Report, issued in European Patent Application No. EP 09 00 6908, dated Sep. 3, 2009.

(Continued)

*Primary Examiner* — Hezron E Williams
*Assistant Examiner* — Rodney T Frank
(74) *Attorney, Agent, or Firm* — McDermott Will & Emery LLP (57) ABSTRACT

Provided is a liquid chromatograph system and method configured to accurately obtain measurements by minimizing deviations in measurements due to a transfer from one measurement method to another measurement method. An aspect of the system and method includes minimizing deviations in measurements when a measurement method from a measurement system of a liquid chromatograph is transferred to measurement system under high pressure and high velocity. Such a transfer includes deviations due to differences in analysis conditions. The present subject matter uses a dwell volume value so as to minimize a deviation of measurement result due to methods before and after transfer. Another aspect includes calculating a correction value when there is a deviation in the measurement result, and automatically reflecting the correction value for the method transfer.

2 Claims, 5 Drawing Sheets

U.S. PATENT DOCUMENTS

| | | | |
|---|---|---|---|
| 2003/0110000 A1 | 6/2003 | Quimby et al. | |
| 2004/0122611 A1 | 6/2004 | Quimby et al. | |
| 2004/0224425 A1* | 11/2004 | Gjerde et al. | 436/518 |
| 2006/0273011 A1* | 12/2006 | Larson | 210/656 |
| 2007/0074766 A1* | 4/2007 | Klee et al. | 137/487.5 |
| 2008/0264491 A1* | 10/2008 | Klee et al. | 137/9 |

FOREIGN PATENT DOCUMENTS

| | | |
|---|---|---|
| DE | 197 14 273 A1 | 11/1997 |
| EP | 0 570 707 A2 | 11/1993 |
| JP | 2003-194795 | 7/2003 |
| JP | 2006-201064 | 8/2006 |
| WO | WO 01/77662 A2 | 10/2001 |

OTHER PUBLICATIONS

John. W. Dolan, "Dwell Volume Revisited", Chromatography Online.com, May 1, 2006, Advanstar.

Japanese Notice of Rejection, w/ partial English translation thereof, issued in Japanese Patent Application No. JP 2008-134904 dated Sep. 13, 2011.

* cited by examiner

| | A | B | C | D | E | F | G | H | I |
|---|---|---|---|---|---|---|---|---|---|
| 1 | REFERENCE TIME PROGRAM TABLE | | | | NEW TIME PROGRAM TABLE | | | | |
| 2 | Time [min] | %B | | | Time [min] | %B | FLOW RATE [ml/min] | | |
| 3 | 0.0 | 10.0 | | | | | | | |
| 4 | 10.0 | 90.0 | | | | | | INPUT CONTENT CHECK | |
| 5 | 15.0 | 90.0 | | | | | | | |
| 6 | 15.1 | 10.0 | | | | | | | |
| 7 | 20.0 | 10.0 | | | | | | ERASE ALL | |
| 8 | | | | | | | | | |
| 9 | | | | | | | | | |
| 10 | | | | | | | | ERASE OUTPUT CONTENT | |
| 11 | | | | | | | | | |

(40 = REFERENCE TIME PROGRAM TABLE; 41 = NEW TIME PROGRAM TABLE)

Sheet tabs: TIME PROGRAM TABLE / FOR PRINTER USE

FIG. 6

WAY OF METHOD TRANSFER OF LIQUID CHROMATOGRAPH AND LIQUID CHROMATOGRAPH SYSTEM

CLAIM OF PRIORITY

The present application claims priority from Japanese Patent Application No. 2008-134904 filed on May 23, 2008, the content of which is hereby incorporated by reference into this application.

BACKGROUND OF THE INVENTION

1. Field of the Invention

The present invention relates to a way of method transfer of liquid chromatograph and a liquid chromatograph system.

2. Description of the Related Art

An analytic technology utilizing a liquid chromatograph system (herein below will be called as liquid chromatography is required to be highly accurate.

In order to obtain highly accurate data of liquid chromatograph, a transfer of method is enumerated.

The method implies the technical conditions set in an liquid chromatograph, when liquid chromatograph is measured and includes, for example, such as flow rate, injection amount and pressure limit.

Conventionally, as disclosed in Japanese patent document JP-A-2003-194795, a transfer of method was performed in such a manner that after correcting time axis, local data are caused to match with respect to a reference value having a same time scale or after transferring time axis, the data are caused to correspond to a reference value based on a different time scale.

However, a transfer of the method, when an analysis is performed under a condition where a linear velocity (which represents a velocity when a certain component passes through a column) is faster than a conventional one (for example, a linear velocity of a few times faster than a conventional velocity), has been performed according to knowhow and the like based on experiences until now, and no considerations with regard to improving accuracy have been given particularly.

SUMMARY OF THE INVENTION

A feature of the present invention is to transfer a certain liquid chromatograph method (first method) to another method (second method) under a condition in which the linear velocity is faster than that in the first method.

Another aspect of the present invention is to use data of a column (for example, such as an inner diameter of the column, length of the column and diameter of particle) for the transfer of the method.

Still another aspect of the present invention is to use a dwell volume (a volume representing that of from the portion where eluent is mixed to a column inlet) for the transfer of the method in order to reduce a deviation of measurement results by the methods before and after the transfer.

Further aspect of the present invention is to calculate a correction value from measurement data for correcting the measurement result and to use the correction value for the transfer of the method.

Still further aspect of the present invention is to use at least one of a linear velocity (which represents a velocity when a certain component passes through a column) and a pressure (which represents a hydrostatic pressure applied at a pump outlet) of the method after transfer that is set in advance for the transfer of the method.

According to the present invention, a certain method of liquid chromatograph can be transferred in high accuracy to another method that is operated under a further high velocity condition.

DESCRIPTION OF THE PREFERRED EMBODIMENTS

At first, a way of method transfer will be explained and then a mode for performing the transfer in high accuracy will be explained.

Embodiment 1

Herein below, embodiment 1 of the present invention will be explained with reference to the drawings.

Figure 1:
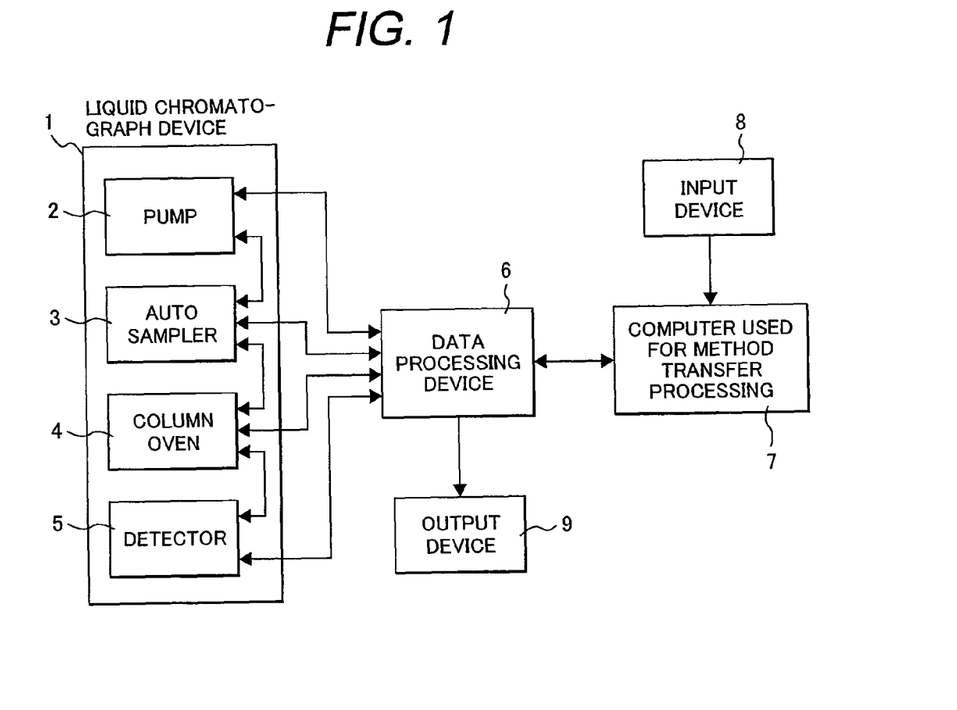
FIG. 1 is a system configuration diagram showing embodiment 1 of the present invention.

FIG. 1 shows a system configuration of the present invention. A liquid chromatograph device 1 is constituted by a pump 2, an auto sampler 3, a column oven 4, a detector 5, a data processing device 6, a method transfer processing computer 7, an input device 8 and an output device 9. From the input device 8 parameters of a method that is an object for transfer are input from the input device 8 to the method transfer processing computer 7 and the method transfer is performed therein. At the time of analysis, commands calculated and set by the method transfer processing computer 7 are issued from the data processing device 6, and a group of parameters are transmitted to the pump 2, the auto sampler 3, the column oven 4 and the detector 5. Measured values of respective components detected by the detector 5 are fetched by the data processing device 6 and an analysis result is transmitted to the output device 9.

Further, the function of the method transfer processing computer 7 can be incorporated into the data processing device 6.

Figure 2:
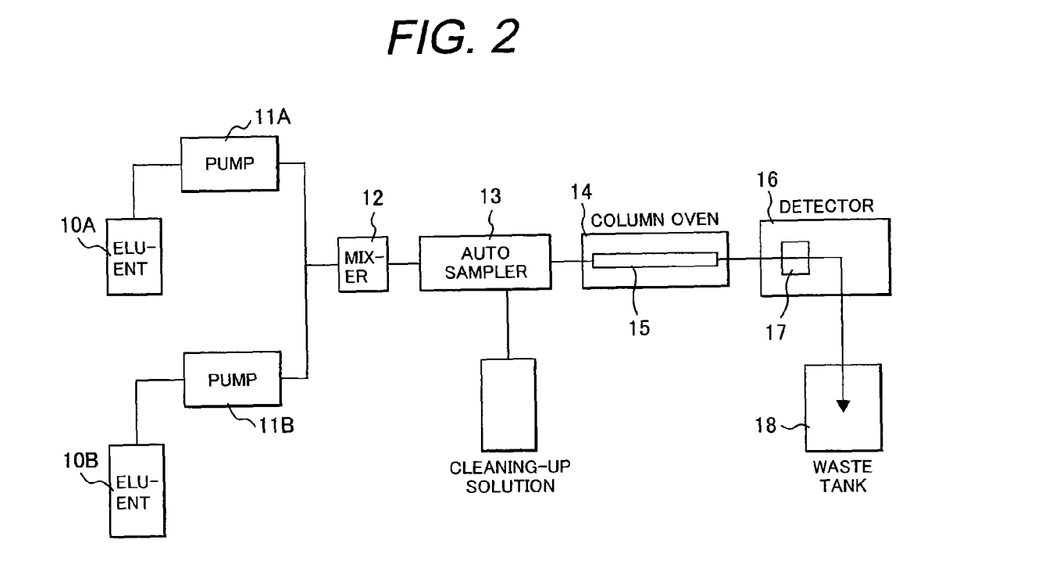
FIG. 2 is a flow line diagram of the system showing embodiment 1 of the present invention.

FIG. 2 shows an example of flow line configurations of the present invention applied to the gradient analysis. Eluent 10A and 10B are respectively sucked by pumps 11A and 11B and are transferred after mixed to a column oven 13 via an auto sampler 13. A sample is injected from the auto sampler 13 and transferred to an column 15. Respective solutes in the sample are separated and developed by the eluent (mobile phase) 10A or 10B in the column (stationary phase) 15. Detention time of these solutes are different depending on separation ratio thereof existing in the mobile phase or the stationary phases. In order to stabilize the detention time of the respective solute, the column 15 is held in a constant temperature by utilizing the column oven 14. The respective solutes separated and developed reach a cell 17 in a detector 13 while having differences with regard to the detention times and are wasted to a waste tank 18.

Lists of parameters used for the measurement transfer are shown in Tables 1 and 2. Now, a calculation of method transfer will be explained.

TABLE 1

| | | Input | | |
|---|---|---|---|---|
| No. | Parameters | liquid chromatograph | Ultra high-speed liquid chromatograph | Output |
| 1 | Column inner diameter | $D_0$ | $D_1$ | |
| 2 | Column length | $L_0$ | $L_1$ | |
| 3 | Particle diameter | $d_0$ | $d_1$ | |
| 4 | Flow rate | $F_0$ | | F |
| 5 | Injection amount | $V_0$ | | V |
| 6 | Pressure | $P_0$ | $P_{limit}$ | P |
| 7 | Linear velocity | | f | |
| 8 | Time program | Table 2 | | Table 2 |

TABLE 2

| | | Input | | |
|---|---|---|---|---|
| No | Parameters | liquid chromatograph | Ultra high-speed liquid chromatograph | Output |
| 1 | Time | $T_0$ | | T |
| 2 | % B | $B_0$ | | B |

At first, when shifting an analysis method from a liquid chromatograph column to a ultra high-speed liquid chromatograph column, a flow rate is calculated so that a linear velocity of the ultra high-speed liquid chromatograph column becomes equal to that of the liquid chromatograph. Since even when column particle diameters are different, porosity is generally constant, and although the column length has a correlation with the pressure loss and the theoretical plate number, but has no direct correlation with the linear velocity.

Subsequently, a primary pressure value of the ultra high-speed liquid chromatograph column is calculated based on the column length, particle diameter and the pressure value of the liquid chromatograph column. Then, by using the pressure limit value ($P_{limit}$ in Table 1) of the ultra high-speed liquid chromatograph as a target, the flow rate is pulled up. In the present invention, as the pressure limit value 80% of a set value is selected. For example, when 50 MPa is set for the pressure limit, the flow rate is pulled up to 40 MPa corresponding to 80% thereof as the target.

Subsequently, calculation of gradient time program is performed. In this invention, the term "gradient time program" means the control program of eluent mixing ratio as a function of time. When the linear velocity is constant, time required when the sample passes through the column is proportional to the column length, the gradient time program also assumes a proportional relationship with the column length. When the linear velocity is pulled up, the time for the gradient time program becomes to anti-proportional to the linear velocity.

Further, when a volume inside a column becomes small, since a delay of gradient elution cannot be neglected, a value of a dwell volume is incorporated in a calculation of time program.

Herein below, output items for the method transfer and equations for the calculation will be explained.

(1) Flow Rate F

The flow rate F in the method for the ultra high-speed liquid chromatograph is calculated from a product of a square of inner diameter ratio of the columns of the ultra high-speed liquid chromatograph and the liquid chromatograph and the flow rate of the method for the liquid chromatograph. This is shown in equation (1).

$$F = F_0 \left(\frac{D_1}{D_0}\right)^2 \quad (1)$$

Herein, $F_0$ is the flow rate in the method for the liquid chromatograph, $D_0$ is the column inner diameter for the liquid chromatograph and $D_1$ is the column inner diameter for the ultra high-speed liquid chromatograph.

Herein below, the equation (2) for calculation when the flow rate is pulled up while considering the pressure limit is shown below.

$$F = \left(\frac{D_1}{D_0}\right)^2 \times F_0 \times f \quad (2)$$

(2) Sample Injection Volume V

The sample injection volume V in the method for the ultra high-speed liquid chromatograph is calculated from a product of a square of inner diameter ratio of the columns of the ultra high-speed liquid chromatograph and the liquid chromatograph and the sample injection volume of the method for the liquid chromatograph. This is shown in equation (3).

$$V = \left(\frac{D_1}{D_0}\right)^2 \times V_0 \quad (3)$$

Herein, $V_0$ shows the sample injection volume of the method for the liquid chromatograph, $D_0$ is the column inner diameter for the liquid chromatograph and $D_1$ is the column inner diameter for the ultra high-speed liquid chromatograph.

(3) Pressure P

The pressure P in the method for the ultra high-speed liquid chromatograph is calculated from a product of a square of inner diameter ratio of the columns of the ultra high-speed liquid chromatograph and the liquid chromatograph, a flow rate ratio thereof, a column length ratio thereof and a square of column particle diameter ratio thereof. This is shown in equation (4).

$$P = P_0 \times \left(\frac{D_0}{D_1}\right)^2 \times \frac{F_1}{F_0} \times \frac{L_1}{L_0} \times \left(\frac{d_0}{d_1}\right)^2 \quad (4)$$

Herein, $P_0$ is a pressure of the method for the liquid chromatograph, $D_0$ is the column inner diameter for the liquid chromatograph, $D_1$ is the column inner diameter for the ultra high-speed liquid chromatograph, $F_0$ is the flow rate for the liquid chromatograph, $F_1$ is the flow rate for the ultra high-speed liquid chromatograph, $L_0$ the column length for the liquid chromatograph, $d_0$ is the particle diameter for the liquid chromatograph and $d_1$ is the particle diameter for the ultra high-speed liquid chromatograph.

(4) Time Program T

First, the case wherein the pressure limit and the dwell volume are not considered will be explained in equation (5). The value of the time program is in a proportional relationship with the column length.

$$T = T_0 \left( \frac{L_1}{L_0} \right) \quad (5)$$

Next, the case when only the dwell volume is considered is shown in equation (6).

$$(T + T_{delay1}) = (T_0 + T_{delay0}) \times \frac{L_1}{L_0} \quad (6)$$

Herein, T shows a time program for the ultra high-speed liquid chromatograph, $T_0$ is a time program for the liquid chromatograph, $T_{delay0}$ is a dwell volume for the liquid chromatograph and $T_{delay1}$ is a dwell volume for ultra high-speed liquid chromatograph. $T_{delay0}$ is calculated according to the following equation (7).

$$T_{delay0} = \frac{\text{The volume of the mixer of the original method } (\mu l)}{F_0 \times 1000} \quad (7)$$

In the equation (7), "The volume of the mixer of the original method" is a value of dwell volume for the liquid chromatograph. $F_0$ is the flow rate for the liquid chromatograph. $T_{delay1}$ is calculated according to the following equation (8).

$$T_{delay1} = \frac{\text{The volume of the mixer of the new method } (\mu l)}{F \times 1000} \quad (8)$$

In the equation (8), "The volume of the mixer of the new method" is a value of dwell volume for the ultra high-speed liquid chromatograph. F is a flow rate for the ultra high-speed liquid chromatograph.

Then, the case wherein only the pressure limit is considered will be explained. A value of the time program is proportional to the column length and is anti-proportional to the pulled up linear velocity. This is shown in equation (9).

$$T = T_0 \times \frac{1}{f} \times \left( \frac{L_1}{L_0} \right) \quad (9)$$

At last, the case wherein the pressure limit and the dwell volume are considered will be explained. The value of the time program is affected by the dwell volume as well as is anti-proportional to the pulled up linear velocity. The formula for the calculation when assumed the linear velocity as f is shown in equation (10).

$$(T + T_{delay1}) = (T_0 + T_{delay0}) \times \frac{1}{f} \times \frac{L_1}{L_0} \quad (10)$$

The $T_{delay0}$ and $T_{delay1}$ are those shown in the previous equations.

Figure 3:
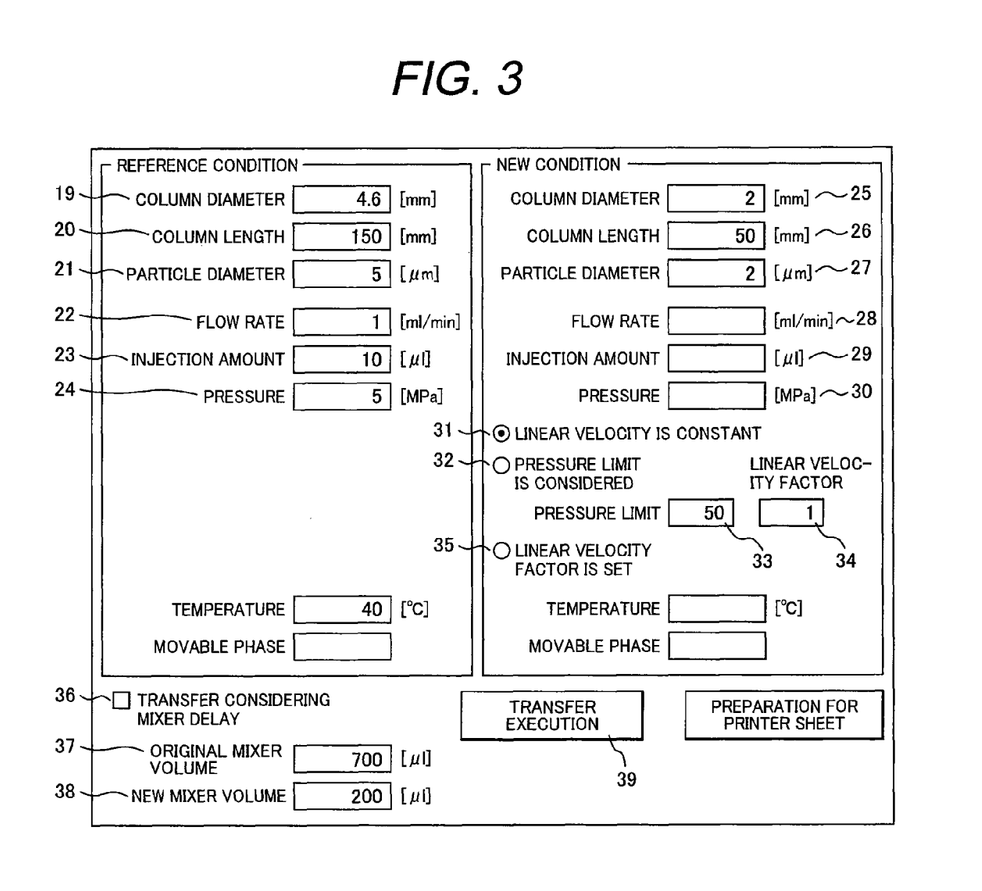
FIG. 3 is a operating panel for a method transfer showing embodiment 1 of the present invention.
Figure 4:
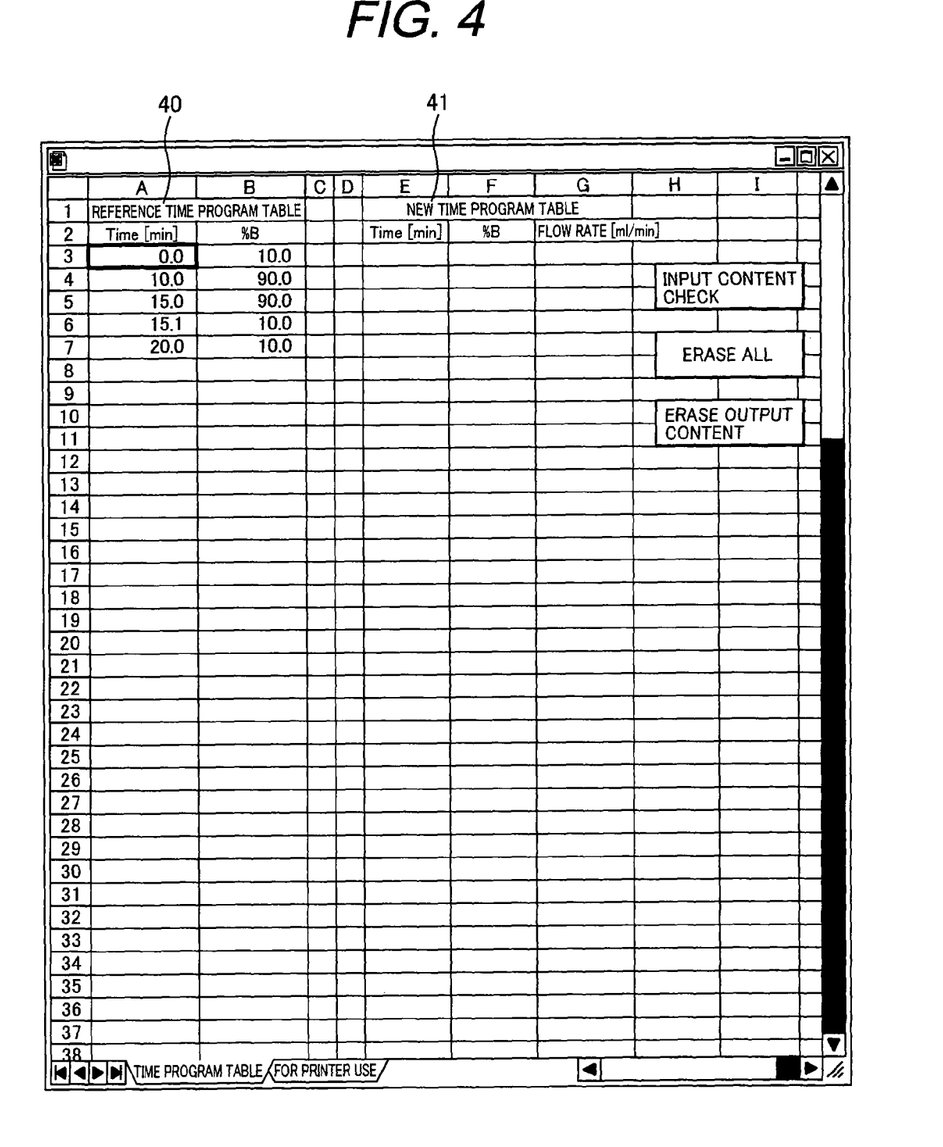
FIG. 4 is a operating panel for a method transfer showing embodiment 1 of the present invention.

FIGS. 3 and 4 show the operating panel representing a computer program tool used for the method transfer that automatically perform the above process (1)~(4). The tool includes a form portion as shown in FIG. 3 in which parameters such as a flow rate and an injection volume are input, and a sheet portion as shown in FIG. 4 in which the gradient time program is input.

In the form portion as shown in FIG. 3, set values of the method before transfer are input in the corresponding dialog boxes such as a column inner diameter 19, a column length 20, a particle diameter 21, a flow rate 22, an injection volume 23 and a pressure 24. The values of a column used in the measurement system after the transfer are set in the dialog boxes for a column diameter 25, a column length 26 and a particle diameter 27. A flow rate 28, an injection amount 29 and a pressure 30 are also provided in these dialog boxes.

When the linear velocities before and after transfer are set equal, a radio button 31 for "linear velocity is constant" is selected.

When the linear velocity is pulled up while considering the pressure limit, a radio button 32 for "pressure limit is considered" is selected, and a limit value of the pressure is set at a pressure limit box 33. A target linear velocity is pulled up to 80% of the value set at the pressure limit box 33.

When directly designating a linear velocity multiplying factor, a radio button 35 for "linear velocity factor is set" is selected and the multiplying factor is set at a linear velocity factor box 34.

When performing a correction with regard to the dwell volume, a check box 36 for "transfer considering mixer delay" is selected and a dwell volume in the measurement system before transfer is set at a original mixer volume box 37. Further, a dwell volume in the measurement system after transfer is set at a new mixer volume box 38.

Settings of time programs are performed at a sheet portion as shown in FIG. 4. A time program of the method before transfer is set at a reference Time Program Table 40.

After completing the setting, when a transfer execution button 39 is pressed, a flow rate 28, an injection volume 29 and a pressure 30 in the measurement system after transfer are calculated. Further, transferred values of time program are output at a new Time Program Table 41.

Figure 5:
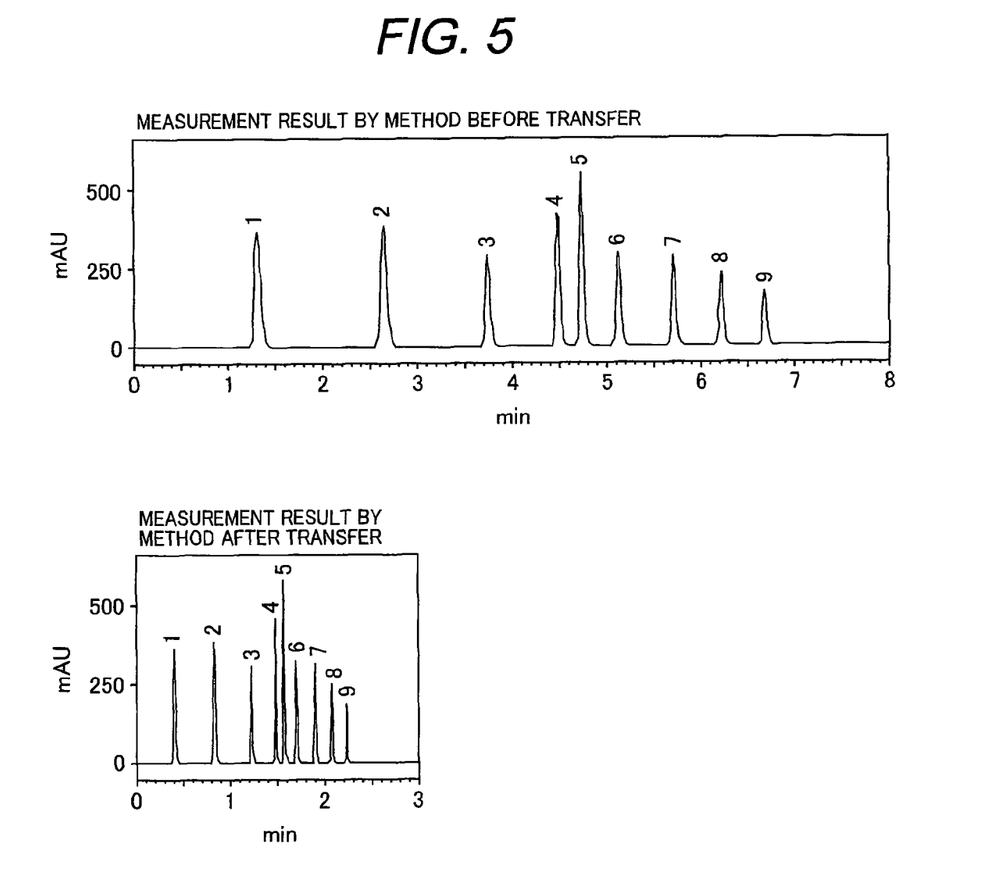
FIG. 5 is a measurement example before and after transfer for explaining embodiment 1 of the present invention.

FIG. 5 shows an example of measurement data (chromatogram) obtained by using methods before and after transfer. Columns having a same performance were used before and after transfer and the measurement was performed at 3 times higher velocity (linear velocity "3").

The gradient corresponding to the peak in FIG. 5 are as follows.

1: Acetanilide
2: Acetophenone
3: Propiophenone
4: Butirophenone
5: Benzophenone
6: Valerophenone
7: Hexanophenone
8: Heptanophenone
9: Octanophenone A list of parameters of the method is shown in Table 3. Settings of gradient time program before transfer is shown in Table 4 and settings of gradient time program after transfer is shown in Table 5. Further, retention time ratio of respective peeks are shown in Table 6.

TABLE 3

| Item to be set | Method before transfer | Method after transfer |
|---|---|---|
| Column inner diameter [mm] | 2 | 2 |
| Column length [mm] | 50 | 50 |
| Particle diameter [mμ] | 2 | 2 |
| Flow rate [ml/min] | 0.2 | 0.6 |
| Injection volume [μl] | 2 | 2 |
| Pressure [Mpa] | 9 | 27 |
| Linear velocity | | 3 |
| Mixer volume [μl] | 700 | 300 |

TABLE 4

| Time [min] | % B |
|---|---|
| 0.0 | 65 |
| 5.0 | 5 |
| 5.1 | 65 |
| 8.0 | 65 |

TABLE 5

| Time [min] | % B |
|---|---|
| 0.0 | 65 |
| 1.7 | 5 |
| 1.8 | 65 |
| 3.0 | 65 |

TABLE 6

| Retention time ratio | Method before transfer | Method after transfer |
|---|---|---|
| $t_2/t_1$ | 2.02 | 2.02 |
| $t_3/t_2$ | 1.42 | 1.45 |
| $t_4/t_3$ | 1.21 | 1.20 |
| $t_5/t_4$ | 1.06 | 1.07 |
| $t_6/t_5$ | 1.08 | 1.08 |
| $t_7/t_6$ | 1.11 | 1.12 |
| $t_8/t_7$ | 1.09 | 1.09 |
| $t_9/t_8$ | 1.08 | 1.09 |

The retention time ratio $t_2/t_1$ shows a retention time ratio of No. 1 and No. 2 peeks. Under a same analysis condition, it is considered as desirable that an accuracy of retention time value in a measurement of a certain component is below 3%. Although since the measurement systems are different with regard to the methods before and after transfer in the present invention, it is not said that the measurement is performed under a same analysis condition, however, the above value is used as an index for an accuracy evaluation of the retention time. In the methods before and after transfer, since the accuracy of the retention time ratios between respective peeks are all below 3%, a good result is maintained.

Embodiment 2

As embodiment 2, an embodiment is shown wherein when the retention time ratios differ, the flow rate and the time for the gradient time program are shifted in order to correct the deviation.

Figure 6:
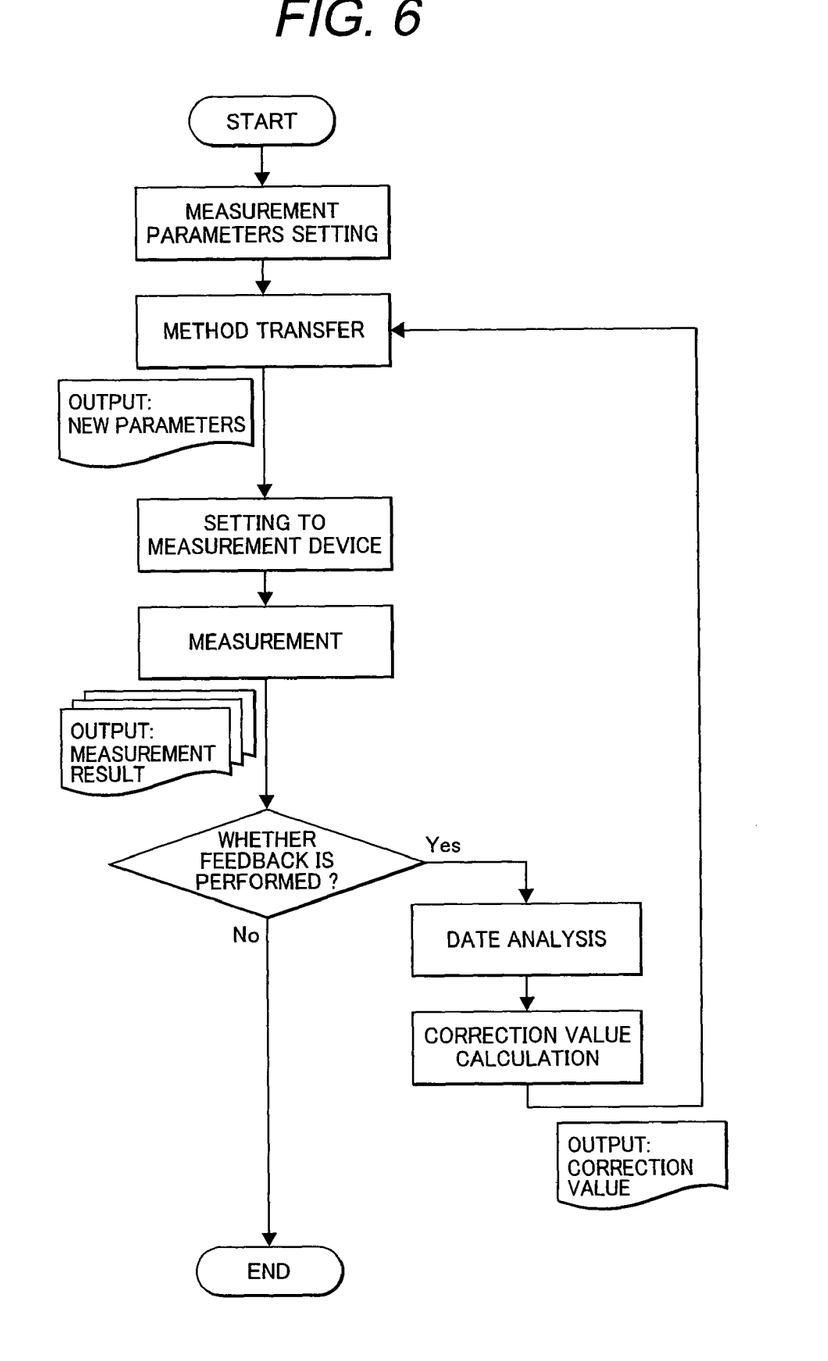
FIG. 6 is a flowchart of an operation according to embodiment 2 of the present invention.

A flowchart of an operation performed according to the present embodiment is shown in FIG. 6.

By the measurement with the method before transfer, the retention times of the measurement components become clear. When assuming a retention time of a certain component before transfer as tx and a retention time of the same component obtained by the method after transfer as ty, the flow rate is corrected as follows so as to match the retention times.

$$F=(f \times ty) \div tx$$

Wherein, f shows a linear velocity. In association with this, the gradient time program is also shifted by the flow rate correction component from a formula for the calculation.

In Table 3, for example, an instance when the holding time ratio of No. 2 peek is matched will be considered. The holding time of No. 2 peek with the method before transfer is 2.65. That with the method after transfer is 0.85. Thereby, the value of the flow rate is corrected to 0.85×3/2.65 times. The values of the time program are respectively shifted by the flow rate correction component from the equation for the calculation of the time program.

Although the present invention is particularly advantageous for a transfer and optimization of method from a liquid chromatograph to a super high speed liquid chromatograph, but not limited to the above embodiments and can be modified other than the above within the spirit of the present invention. For example, through setting the linear velocity f to a value below 1 and setting the items such as column length and the particle diameter properly, a transfer from a method under a condition of a high velocity and a high pressure to a method under a general purpose condition can be effected.

The invention claimed is:

1. A liquid chromatograph system comprising:
an injecting device for sucking sample solute;
a liquid delivering device for delivering the sample solute;
a column for separating the sample solute;
a detecting device for detecting the separated sample solute;
a first processing device for processing the detection result; and
a panel device for displaying a liquid chromatograph based on the processed result, comprising:
a second processing device for transferring a method, wherein the transfer is from a first method for using a first column to a second method for using a second column based on data of the first column and data of the second column, and
wherein a dwell volume value is used during the transfer.

2. A liquid chromatograph system comprising:
an injecting device for sucking sample solute;
a liquid delivering device for delivering the sample solute;
a column for separating the sample solute;
a detecting device for detecting the separated sample solute;
a first processing device for processing the detection result; and
a panel device for displaying a liquid chromatograph based on the processed result, comprising:
a second processing device for transferring a method, wherein the transfer is from a first method for using a first column to a second method for using a second column based on data of the first column and data of the second column, and
wherein the panel device includes a panel for setting dwell volumes before and after the transfer.

* * * * *